United States Patent
Hinterwaldner et al.

(10) Patent No.: US 6,720,072 B1
(45) Date of Patent: Apr. 13, 2004

(54) HIGH-TEMPERATURE RESISTANT POLYMERIZABLE METAL OXIDE PARTICLES

(75) Inventors: Rudolf Hinterwaldner, Kastanienstrasse 13, D-81547 Müchen (DE); Hans-Juergen Glaesel, Leipzig (DE); Eberhard Hartmann, Priester (DE); Reiner Mehnert, Markkleeburg (DE)

(73) Assignees: Institut fuer Oberflaechermodifizierung E.V. (DE); Rudolf Hinterwaldner (DE)

( * ) Notice: Subject to any disclaimer, the term of this patent is extended or adjusted under 35 U.S.C. 154(b) by 0 days.

(21) Appl. No.: 09/807,008

(22) PCT Filed: Oct. 8, 1999

(86) PCT No.: PCT/EP99/07569
§ 371 (c)(1),
(2), (4) Date: Jul. 6, 2001

(87) PCT Pub. No.: WO00/22052
PCT Pub. Date: Apr. 20, 2000

(30) Foreign Application Priority Data

Oct. 9, 1998 (DE) ......................................... 198 46 660

(51) Int. Cl.[7] .................................................. B32B 5/16
(52) U.S. Cl. ....................................... 428/403; 428/405
(58) Field of Search .................................. 428/403, 405

(56) References Cited

U.S. PATENT DOCUMENTS

| | | | |
|---|---|---|---|
| 3,759,683 A | 9/1973 | Dislich et al. | |
| 3,847,583 A | 11/1974 | Dislich et al. | |
| 4,455,205 A | 6/1984 | Olson et al. | |
| 4,478,876 A | 10/1984 | Chung | |
| 5,494,949 A | * 2/1996 | Kinkel et al. | 523/212 |
| 5,698,309 A | * 12/1997 | Dallmann et al. | 428/323 |
| 6,008,285 A | 12/1999 | Kasemann et al. | |
| 6,261,700 B1 | * 7/2001 | Olson et al. | 428/522 |
| 6,329,058 B1 | * 12/2001 | Arney et al. | 428/403 |

FOREIGN PATENT DOCUMENTS

| DE | 40 20 316 A1 | 1/1992 |
|---|---|---|
| WO | WO 8809776 A1 | 12/1988 |

OTHER PUBLICATIONS

Armin Tauber, et al., "UV and Electron Beam Crosslinked Polyacrylate Nanocomposites", Manuscript of lecture at RadTech, North America 2002, pp. 1–8.

Alain Vidal, et al., "Le greffage sur surfaces solides de molécules organiques et de polyméres", Bulletin De La Societe. Chimique. De. France., 1985, No. 6, pp. 1088–1097, (English abstract).

Larry N. Lewis, et al., "Ultraviolet–Curable, Abrasion–Resistant, and Weatherable Coatings with Improved Adhesion", J. Applied Polymer Science, (1991), vol. 42, pp. 1551–1556.

Hans–Jürgen Gläsel, et al. "Preparation of scratch and abrasion resistant polymeric nanocomposites by monomer grafting onto nanoparticles, 2$^a$", Macromol. Chem. Phys. 2000, 201, No. 18, pp2765–2770.

Frank Bauer, et al., "Preparation of scratch and abrasion resistant polymeric nanocomposites by monomer grafting onto nanoparticles, 1"Macromol. Chem. Phys. 2000, 201, No. 18, pp2654–2659.

E.P. Plueddemann, et al., "New silane coupling agents for reinforced plastics", Modern Plastics 39, Aug. 1962, (8) pp–135, 137, 138, 140, 144, 146, 187, 188, 191, and 193.

Edwin P. Plueddemann, "Adhesion Through Silane Coupling Agents", J. Adhesion, (Jul. 1970), vol. 2, pp. 184–196 and 198, 199 and 201.

John Wiley & Sons, "Coupling Agents", Encyclopedia of Polymer Science and Engineering, 1986, vol. 4, A Wiley–Interscience Publication, pp 284–298.

James V. Crivello, et al., "Preparation and Cationic Photopolymerization of Organic–Inorganic Hybrid Matrixes", Chem. of Mater., 9(7), 1997, pp1562–1569.

R. Kasemann, et al., "Coatings for mechanical and chemical protection based on organic–inorganic sol–gel nanocomposites", New Journal Chemistry, 1994, vol. 18, pp1117–1123.

John D. Blizzard, et al., "Radiation Curable Abrasion Resistant Coatings", Proceedings Rad. Tec., North America 1992, pp 457–461.

* cited by examiner

*Primary Examiner*—H. Thi Le
(74) *Attorney, Agent, or Firm*—Rothwell, Figg, Ernest & Manbeck, PC (57) ABSTRACT

High-temperature resistant polymerizable metal oxide particles having a glass transition temperature of the homopolymerizable $\geq 100°$ C. and a core A. The core includes an oxide of a metal or semimetal of the third to sixth main group, of the first to eighth subgroup of the periodic table, or of the lanthanides, and has at least one group —(B)$_w$—X bound via the oxygen atom of the oxide or hydroxide, in which B represents a binding link, and X represents a reactive functional group, and w is equal to 0 or 1. The inventive particles are useful, in particular, for producing coating materials, molding materials and adhesives.

19 Claims, 4 Drawing Sheets

HIGH-TEMPERATURE RESISTANT POLYMERIZABLE METAL OXIDE PARTICLES

FIELD OF THE INVENTION

The present invention relates to high temperature resistant polymerizable metal oxide particles, to processes for preparing them, to compositions comprising said particles, and to their use.

DESCRIPTION OF RELATED ART

Nanoscale inorganic materials (materials having an average article size in the nanometer range) with surface modification by organic radicals are already known; see the prior art discussed in more detail below. The known nanoscale materials, including the preparation processes, have a number of disadvantages which restrict their use almost exclusively to the application of hard layers to substrate surfaces. The reasons for these disadvantages lie predominantly in the preparation of the materials by the sol-gel process. The sol-gel process is described, for example, in C. J. Brinker and G. Scherer "Sol-Gel-Science—The Physics and Chemistry of Sol-Gel-Processing", Academic Press, New York (1989), and also in DE 1941191 A, DE 3719339 A and DE 4020316 A. In the sol-gel process, inorganic particles, such as aqueous colloidal silicon dioxide solutions (water glass), are reacted with alkoxysilanes via hydrolysis and condensation reactions, giving gels having different or even divergent properties.

The properties of the particles obtained by the sol-gel process may be altered by modifying the surface. The reaction of colloidal silicon dioxide by the sol-gel process with acrylated alkoxysilanes in an inert organic solvent, and the use of the resulting products to produce scratch resistant coatings, for instance, have already been described; see, for example, U.S. Pat. No. 4,455,205, U.S. Pat. No. 4,478,876, and Proceedings RadTech, North America '92, pages 457–461 (1992). A similar procedure has been taken for the introduction of functional groups into radiation curable sol-gel coatings; see New J. Chem. 18, 1117–1123 (1994) and DE 4338361 A. Furthermore, Chem. Mater. 9, 1562–1569 (1967) describes the modification of colloidal silicon dioxide with a trialkoxysilane containing epoxy or 1-propenyl ether groups, in anhydrous, liquid organic phase.

The particles prepared by the sol-gel process possess the following disadvantages:

They lack reproducible structures and properties.
Their preparation is costly and not always environment-friendly.
The storage stabilities are unsatisfactory.
There are no possibilities, or only limited possibilities, for their copolymerization with other monomers.
The amount of particles which may be taken up into substrates, such as coating materials, etc., is limited.

The use of the particles obtained by the sol-gel process is therefore limited in practice to the production of hard, scratch resistant coatings.

BRIEF SUMMARY OF THE INVENTION

It is now an object of the present invention to provide particles and processes for their preparation which do not have at least one of the abovementioned disadvantages. In particular, the intention is to provide particles which are simpler and more economic to prepare and which are also suitable for high temperature application.

It has surprisingly now been found that this object is achieved if the particles are prepared by a process in which the starting material is not a sol but instead the particles are used as solids and the surface is modified and covalently bonded by reaction with appropriate reagents.

The present invention accordingly provides high temperature resistant polymerizable metal oxide particles having a glass transition temperature of the homopolymers of $\geq 100°$ C. and having a core A comprising at least one oxide of a metal or semimetal from main groups three to six, transition groups one to eight of the periodic system, or the lanthanides and having at least one group $—(B)_w, —X$, which is bonded covalently to the core by way of one or more oxygen atoms of the oxide or hydroxide, w being 0 or 1 and B being a radical of the formulae in which x is from 0 to 100, y1, y2 and z independently of one another are 0 or 1, and Me is a metal or semimetal from main groups three to six or transition groups three to eight of the periodic system, the free valances of Me representing a bond to a further oxygen atom of the core A and/or a bond via an oxygen atom to an Me in another group B or and/or a bond to an oxygen atom of another core A and/or being satisfied by H, an organic radical and/or a trialkylsilyloxy radical;

R is divalent alkyl, cycloalkyl, aryl, arylalkyl, alkylaryl, alkoxy, acyl, acyloxy or a radical remaining following the removal of two phenolic hydrogen atoms from a phenol compound having at least two phenolic hydroxyl groups, it being possible for R to be substituted, if desired, by 1, 2 or 3 radicals selected independently of one another from hydroxy, alkoxy, halogen and also, in the case of aryl or cycloalkyl radicals, alkyl, and/or interrupted in the chain by one or two oxygen atoms, and X is a reactive functional group or a radical containing a reactive functional group.

The invention further relates to a process for preparing the high temperature resistant, polymerizable metal oxide particles, in which the radicals B, B—X or X are covalently bonded to the core A, present in solid form, in the presence of a strong acid.

DETAILED DESCRIPTION OF THE INVENTION

In the context of the present invention, the following provisions apply:

Alkyl (both alone and in alkoxy, alkylaryl, etc.) is a straight-chain or branched alkyl group having preferably from 1 to 50 carbon atoms, with particular preference from 1 to 20 carbon atoms, in particular from 1 to 12 carbon atoms, and with very particular preference from 1 to 8 carbon atoms. Examples of alkyl groups are methyl, ethyl, n-propyl, i-propyl, n-butyl, i-butyl, sec-butyl, t-butyl, n-hexyl, n-dodecyl and stearyl.

Cycloalkyl is preferably $C_3$–$C_8$ cycloalkyl, especially $C_5$–$C_7$ cycloalkyl. Examples of cycloalkyl groups are cyclopropyl, cyclobutyl, cyclopentyl, cyclohexyl and cycloheptyl, cyclopentyl and cyclohexyl being preferred.

Aryl (both alone and in arylalkyl or alkylaryl) is preferably phenyl or naphthyl.

Preferred arylalkyl groups are benzyl or phenethyl.

Preferred alkylaryl groups are o-, m- or p-tolyl or -xylyl.

Examples of alkoxy groups are methoxy, ethoxy, n-propoxy, i-propoxy, n-butoxy, t-butoxy, etc.

Acyl is a straight-chain or branched alkyl- or arylcarbonyl group having preferably from 1 to 50 carbon atoms or from 1 to 18 carbon atoms, in particular from 1 to 12 carbon atoms, and with particular preference from 1 to 6 carbon atoms. Examples of acyl groups are formyl, acetyl, propionyl, butyryl, benzoyl, etc. Corresponding provisions apply to acyloxy. Examples of acyloxy are, in particular, acetyloxy, propionyloxy and benzoyloxy.

In the case of the divalent radicals R, both bonding sites are located at an arbitrary point in the alkyl, cycloalkyl, aryl or acyl radical. In the case of divalent arylalkyl and alkylaryl, one bonding site is located in the aryl moiety and the other in the alkyl moiety. In the case of divalent acyl and acyloxy, one bonding site is located in the alkyl or aryl moiety and the other on the carbonyl carbon atom or on the oxygen atom, respectively. Divalent acyl and acyloxy is incorporated into the group B preferably in such a way that the alkyl or aryl radical is connected to Me or, respectively, to the oxygen atom of $Me(O)_{y2}$.

A feature of the particles of the invention is that they have a large number of side chains —$(B)_w$—X. The number of side chains is greater than 2 and is generally in the range from 10 to 100, preferably from 10 to 50, and in particular from 20 to 50. The amount of side chains —$(B)_w$—X, based on the overall weight of the particles, is generally at least 10% by weight, preferably at least 20% by weight, and with particular preference at least 50% by weight. The side chains may account for up to 90% by weight, preferably up to 75% by weight, of the particles.

The average particles size (determined by means of scanning electron microscopy) of the particles of the invention may be up to 1 mm. In general, it is in the range from 1 nm to 0.5 mm, advantageously in the range from 1 to 500 nm, preferably from 1 to 300 nm, or from 1 to 100 nm, in particular from 10 to 50 nm. The specific surface area (BET, determined in accordance with DIN 66131) is generally in the range from 50 to 400 $m^2$/g, preferably from 70 to 300 $m^2$/g.

The glass transition temperature of the homopolymers of the particles of the invention is $\geq 100°$ C., advantageously $\geq 150°$ C., preferably $\geq 250°$ C., in particular $\geq 350°$ C. and with particular preference $\geq 400°$ C. The upper limit is generally at 600° C., preferably at 500° C.

The core A of the particles of the invention is formed of an oxide of at least one metal or semimetal from main groups three to six, from transition groups one to eight of the periodic system, or of the lanthanides. The expression oxide also embraces hydroxides and (mixed) oxide-hydroxides. It is possible to employ mixtures of different oxides or mixed oxides. The surface of the core has hydroxyl groups by way of which the side chains —$(B)_w$—X are attached.

The core A likewise comprises particles whose sizes and surface areas are within the stated ranges given above for the particles of the invention.

Suitable oxides for the core A are preferably the oxides of the following metals or semimetals:

Main group three: B, Al, Ga;

Main group four: Si, Ge and Sn;

Main group five: As, Sb and Bi;

Main group six: Te;

Transition group one: Cu;

Transition group two: Zn, Cd;

Transition group three: Sc, Y, La;

Transition group four: Ti, Zr, Hf;

Transition group five: V, Nb;

Transition group six: Cr, Mo, W;

Transition group seven: Mn;

Transition group eight: Fe, Co, Ni;

Lanthanides: Ce, Yb, Lu.

Preference is given to the oxides of metals or semimetals from main groups three and four and from transition groups one, four, six and eight of the periodic system, and also mixtures and mixed oxides thereof.

Particular preference is given to the oxides of Si, Al, Ti, Zr, and mixtures and mixed oxides thereof.

The side chains of the particles of the invention are formed by the functional group X (if w=0) or by radicals of the formulae:

$$—(MeO)_x Me(O)_{y1}—(R)_{y2}—X \text{ or } —R(O)_z—X$$

in which x, y1, y2 and z and also Me possess the definitions given above. The metals or semimetals Me may be identical or different. Preferably, Me is one of the metals or semimetals stated above as being preferred for the core A. x is preferably from 0 to 10, in particular 0, 1, 2, 3 or 4, and with particular preference 0, 1 or 2.

B is preferably selected from the following radicals:

a) —Me $(O)_{y1}$—R— b) —Me—O—$Me(O)_{y1}$—R— c) —Me—O—Me—O—$Me(O)_{y1}$—R— d) —R—O— e) —R— in which y1 is 0 or 1 and R possesses the definitions indicated above.

Moreover, —Me—O—Me— in the radical b) is preferably selected from:

—Si—O—Si—

—Si—O—Al—

—Si—O—Ti—

—Si—O—Zr—

—Al—O—Ti—

—Al—O—Zr—

—Al—O—Al— and —Me—O—Me—O—Me— in the radical c) is preferably —Si—O—Ti—O—Zr—.

The sequence of different metal atoms in the radical —$(MeO)_x Me(O)_{y1}$—$(R)_{y2}$— is arbitrary. Attachment to the core may take place by way of one or the other metal atom, e.g., —Si—O—Al— may be incorporated into the side chain in such a way that the attachment to the core is either by way of the Si atom or by way of the Al atom.

The metals and/or semimetals Me may be bonded by way of one or more oxygen atoms of the core. This can be illustrated using the following example where Me is Si:

a)

b)

c)

If the free valences of the Si atom in the structures a) and b) are satisfied by alkoxy groups, a bond to one or two further cores A may take place by alkOH elimination.

The free valences of Me may also represent a bond by way of an oxygen atom to an Me in another group B of the same particle or a different particle, or a bond to an oxygen atom of a different core. In this way, a network is formed, as in a silicon dioxidete or in an aluminosilicon dioxidete, for example. Alternatively, the free valences may be satisfied by an organic radical. Suitable organic radicals are alkyl, alkenyl, cycloalkyl, aryl, arylalkyl, alkylaryl, alkoxy, a group of the formula $R^1COY-$, in which $R^1$ is the radical of an ethylenically unsaturated $C_3-C_8$ monocarboxylic acid or $C_4-C_8$ dicarboxylic acid that remains following removal of the carboxyl group, and Y is O or $NR^2$, where $R^2$ is H or $C_1-C_4$ alkyl, or a group containing phosphorus, especially a group comprising phosphate, pyrophosphate and phosphite groups.

Preferably, the free valences of Me are satisfied by alkyl, aryl, alkoxy, a group of the formula $R^1COY-$, in which $R^1$ and Y possess the definitions indicated above, or a group comprising phosphorus, particular preference being given to groups of the formula $R^1COY-$.

The group of the formula $R^1COY-$ is preferably derived from acrylic acid, methacrylic acid, crotonic acid, sorbic acid, vinylacetic acid, maleic acid, fumaric acid, itaconic acid or citraconic acid, particular preference being given to acrylic acid and methacrylic acid.

The radical R (if present) represents a divalent link to the reactive functional group X. Accordingly, R may be a divalent organic radical attachable to an oxygen atom of the core A or of the segment MeO or to a metal or semimetal Me, on the one hand, and to the reactive functional group, on the other hand. In general, R is the radicals already mentioned above, it being not possible for the alkoxy or acyloxy radical to be bonded to the oxygen atom of one of the abovementioned oxygen atoms of the core or of the groups MeO or R(O). The choice of the group R is guided by the desired properties of the particles and by the nature of the reactive functional group X. Preferred radicals R are divalent alkyl, hydroxyalkyl, alkoxy, acyloxy or a radical remaining after the removal of two phenolic hydrogen atoms from a phenyl compound having at least two phenolic hydroxyl groups. Suitable phenol compounds are bisphenols, as are indicated, for example, in Ullmann's Encyclopedia of Industrial Chemistry 1991, Vol. A 19, page 349. The content of that publication is part of the present specification by reference. Bisphenol A, B or F are preferred.

Further suitable phenol compounds are polymeric phenol compounds, such as resols, novolaks, etc.

If R is a phenol radical, y1 and z are 0.

The reactive functional group is to be capable of entering into chemical reactions with other functional groups either already present in the particles or present externally in coreactants. In particular, it is to be able to enter into a polymerization (including polycondensation and polyaddition) so that crosslinking and/or curing takes place. Reactive groups are, in particular, epoxy groups, isocyanate groups, groups having at least one active hydrogen atom, or groups having at least one ethylenically unsaturated double bond. X may be bonded directly to B or to an oxygen atom of the core; for example, a vinyl group may be bonded to an alkyl group, so that $-(B)_w-X$ is an alkenyl group. Alternatively, X may be attached to B by way of a link Z. Z is generally O, $NR^2$, where $R^2$ is H or $C_1-C_4$ alkyl, OCO, COO, NHCO or CONH. Preferred groups X having an ethylenically unsaturated double bond are thosee of the formula in which $R^1$ is the radical of an ethylenically unsaturated $C_3-C_8$ monocarboxylic acid or $C_4-C_8$ dicarboxylic acid that remains following removal of the carboxyl group, Y is O or $NR^2$ and $R^2$ and $R^3$, which may be identical or different, are H or $C_1-C_4$ alkyl. $R^1$ is preferably derived from acrylic acid, methacrylic acid, crotonic acid, sorbic acid, vinylacetic acid, maleic acid, fumaric acid, itaconic acide and citraconic acid. An example of X is the acrylic or methacrylic group, which is preferably bonded to B by way of O or NH.

One preferred embodiment comprises particles wherein the core A is silicon dioxide, titanium dioxide or an Si/Al mixed oxide, $-B-X$ is $(MeO)_xMe(O)_{y1}$ $(CH_2)_n$ $OCOCR^4=CH_2$ or $(MeO)_xMe(O)_{y1}$ $CH_2CHOHCH_2OCOCR^4=CH_2$, where Me is Si, Al, Ti or Zr, x is 1 or 2, y1 is 0 or 1, n is from 2 to 6 and $R^4$ is H or $CH_3$, the free valences of Si, Al, Ti or Zr being satisfied by alkoxy radicals and/or bonded to oxygen atoms of the same or a different core A.

Groups having active hydrogen atoms are hydroxyl groups, primary and secondary amino groups, thiol groups and silane radicals.

One embodiment with silane radicals comprises particles wherein the side chains are formed by a polyalkyl hydrosiloxane radical (Me=Si; x=30–100; y1 and y2=0; X=H). Particles of this kind may be illustrated by way of example on the basis of the following formula:

A = core
n = 30 to 100, especially 30 to 50

A—O— may be bonded to any desired silane atom. Because of the plurality of silane units, two or more cores may also be bonded to the siloxane chain. Particles of this kind may be used for reaction with silicones and epoxides and as adhesion promoters.

The particles of the invention generally possess two or more side chains. In that case it is possible to incorporate groups X having different reactivity. On the basis of the different reactivity it is possibleie to vary the properties of the particles; for example, materials having dual or even multiple curing functions may be prepared.

The particles of the invention are generally insoluble in water, but may be dispersed in water or in other media in which they are insoluble by means of customary emulsifiers and/or protective colloids. They may also be processed from their melt, since they possess melting and softening points <300° C., preferably <250° C. In comparison to the corresponding products prepared by sol-gel processes, they possess in the melt a substantially improved "heat history", since the inorganic core protects, at least temporarily, the organic constituents in the macromolecule. By the term "heat history" in connection with melt compositions, the skilled worker understands all of the critical parameters which in the course of melting and in the melt cause thermal damage to the organic constituents and thus adversely affect the end properties, such as thermal stability, for example. In this context, see R. Jordan "Schmelzklebstoffe" [Hot-melt adhesives] Vol. 4a (1985) and Vol. 4b (1986), Hinterwaldner-Verlag, Munich. Using the particles of the invention, this "heat history" may be essentially improved and the thermal sensitivity considerably reduced, which is of advantage in particular when compounding and when applying the melt compositions prepared therewith.

Furthermore, the particles of the invention are soluble in inert solvents, such as acetone, methyl ethyl ketone, alcohols (methanol, ethanol, butanols, etc.), ethyl acetate, etc., and also in numerous coreactants which may be brought to reaction with the reactive functional group X. By way of example, the particles are soluble or dispersible in a large number of ethylenically unsaturated monomers, such as vinylaromatic compounds, for example, styrene, esters of acrylic acid or methacrylic acid with $C_1$–$C_{12}$ alkanols or $C_1$–$C_{12}$ alkanediols, e.g., methyl (meth)acrylate, n-butyl (meth)acrylate, t-butyl (meth)acrylate, ethylhexyl (meth)acrylate, acrylonitrile, methacrylonitrile, acrylamide and methacrylamide and also the N—$C_1$–$C_4$-alkylated products thereof, vinyl $C_1$–$C_{18}$ alkyl ethers, esters of vinyl alcohol with $C_1$–$C_{12}$ alkane carboxylic acids, especially vinyl acetate, vinyl propionate, N-vinyllactams, especially N-vinylpyrrolidone, $C_2$–$C_6$ olefins, especially ethylene and propylene, butadiene or isoprene, etc., at least to such an extent that they may be copolymerized with the monomers. The copolymerization produces a polymeric network in which the particles are incorporated by covalent bonding.

The properties of the particles of the invention are also determined by the nature and proportion of the core particles and of the metals and/or semimetals Me in the side chains. As the amount of these components goes up, the high temperature resistance of the particles increases to temperatures above 350° C. and even above 400° C. Tg values of up to zu 600° C. may be achieved. The temperature resistance of such products is generally from 50 to 100° C. above the respective glass transition point. Particularly high temperature resistant materials are obtained by combining Si, Ti and Zr for the metals and/or semimetals in the side chains.

The particles of the invention, through an appropriate choice of the reactive groups, may be reacted with themselves to form homopolymers, but in particular may be reacted with other coreactants to form copolymers, using, for example, the abovementioned ethylenically unsaturated compounds as coreactants. In this way it is possible to vary the properties of the resulting products virtually as desired.

The homopolymerization or the copolymerization with the coreactants takes place in a customary manner known to the skilled worker; for example, by free-radical polymerization if X is ethylenically unsaturated groups or has such a group and if ethylenically unsaturated monomers are used as coreactants. Examples of suitable initiators for the polymerization are organic peroxides and hydroperoxides, such as benzoyl peroxide, t-butyl hydroperoxide, per salts, such as sodium persulfate, sodium peroxodisulfate; hydrogen peroxide; azo compounds, such as azobisisobutyronitril, etc. The free-radical copolymerization may also be initiated by light, for example, UV rays or daylight, in the presence of photoinitiators, or by means of electron beams. Heat curable systems based on epoxides, ethylenically unsaturated compounds and isocyanates are also suitable.

Polyaddition systems are present when one of the components in the system contains epoxy or isocyanate groups and the other component contains groups having active hydrogen atoms. For example, the particles of the invention wherein the reactive group is an epoxy or isocyanate group may be reacted with alcohols or primary or secondary amines, especially polyols and polyamines.

The particles of the invention are prepared starting from the core A, using the chosen oxide in solid, finely divided form. The average particle size and the specific surface area of the core particles are generally within the ranges stated above for the particles of the invention. Core particles which may be used are available commercially, for example, as highly dispersed silicon dioxide, such as Aerosil® from Degussa AG, Frankfurt, HDK 80, 100 and 600 der Wacker-Chemie GmbH, Munich, und Cab-O-Sil® from Cabot Corp., Boston, Mass., USA or highly dispersed titanium dioxide, such as titanium dioxide P25 from Degussa AG. The mixed oxides are also available commercially, e.g., Si—Al mixed oxides under the designation Aerosil® MOX and COK from Degussa AG.

The attachment of the radicals B, —B—X and/or X takes place starting from the core particles in solid form in one process step (in situ) in the presence of strong acids, as was surprisingly found. In general, the material forming the side chain —BX and/or the group —B— is introduced initially and the core particles are incorporated, by stirring, for example. This operation is judiciously conducted at an elevated temperature, generally in the range from 30 to 80° C. Alternatively, the core particles may be impregnated with the material forming the side chains.

If necessary, a reagent capable of bringing about the reaction with the OH groups of the core A is then added to the mixture obtained. In general, said reagent comprises a strong acid, including Lewis acids, which as a catalyst brings about the reaction. The amount of strong acid is generally in the range from 1 to 10% by weight, based on the amount of core particles. Suitable strong acids are organic and inorganic acids, such as sulfuric acid, phosphoric acid, maleic acid, methansulfonic acid or p-toluenesulfonic acid or their anhydrides. Also suitable are dual functional compounds which have at least one acid group and at least one functional crosslinkable organic group in their molecule. Examples thereof are the esters of phosphoric acid with α, β-ethylenically unsaturated carboxylic acids, such as acrylic acid and methacrylic acid. Judiciously, a surfactant (especially an anionic or nonionic surfactant) is added in an amount of in general from 0.1 to 3% by weight, based on the amount of core particles, in order to facilitate the wetting of the core particles.

The reaction is conducted at the abovementioned temperature; the reaction time is generally in the range from 10 minutes to 5 hours. After the end of reaction, the strong acid is neutralized with a base, for example, sodium hydroxide or potassium hydroxide. The salts formed in this case may be removed as desired by means of ion exchangers.

The attachment of the side chain —B—X takes place preferably in one stage by reaction with a compound Y—B—X, where Y is a group capable of reacting with the hydroxide groups on the surface of the core particles. Examples of suitable groups Y are hydroxyl groups, epoxy groups, halogens, organometallic groups, such as trialkoxysilane or trialkoxytitanium compounds, where the free valence of Si and Ti is satisfied by the group B—X. Examples of compounds Y—B—X which may be used are acryloyl- or methacryloyloxypropyl-trimethoxysilane, acryl- or methacryloyloxypropyl-trimethoxytitanium, glycidyl acrylate or glycidyl methacrylate, epoxides having one, especially 2 or more epoxy groups, such as glycidol, mono- and diepoxides based on bisphenol, novolak and cresols, 2,3-epoxypropylurethane having at least one blocked isocyanate group, 2,3-epoxypropyl (meth)acrylate, allyl glycidyl carbonates, glycidyl cyanurates, such as alkoxydiglycidyl cyanurates, alkyl glycidyl ethers and glycerylamines, etc. MeO bridges in the side chain may be introduced by adding the corresponding monomeric or polymeric metal alkoxides or the partial hydrolysis products thereof, examples being tetramethoxysilane, tetraethoxysilane, tetrabutoxytitanium, dimethoxydisilanol, polydimethoxysiloxane, aluminum isopropoxide, etc. The starting compounds required for the introduction of the side chain —B—X are available commercially or may be prepared in a manner known to the skilled worker. The starting compound for the preparation of the particles having a polyalkylhydrosiloxane side chain is also available commercially as Baysilone oil MH 15 from Bayer AG.

Alternatively, the side chain may be introduced in two stages by first introducing the radical B and subsequently connecting the group X to the radical B. The introduction of the radical B takes place by reaction of the core particles with a compound Y—B—Y', in which Y possesses the definitions given above. Y' is a group capable of reacting with the coreactant used to introduce the group X. In general, Y' has the same definitions as Y. Examples of suitable compounds Y—B—Y' are metal alkoxide compounds, such as tetramethoxysilane, tetraethoxysilane, tetrabutoxytitanium, poly(diethoxysiloxane), poly (dimethoxysiloxane), diethoxysiloxane s-butylaluminate, diethoxysiloxane ethyltitanate, poly(dibutyl titanate), poly (octylene glycol titanate), and also the silicon, aluminum and titanium compounds described in DE 4020316 A. These compounds too are available commercially (e.g., from Kenrich Petrochemicals Inc., Bayonne, N.J., USA or Gelest, Inc., Tullytown, Pa., USA) or may be prepared in a manner known to the skilled worker.

Then, in a further step, the product obtained is reacted with a reagent for introducing the functional group X. Examples of suitable reagents are metal alkoxides, where one valence of the metal is satisfied with the functional group. Examples of such compounds are isopropyl dimethacryloyl isostearoyl titanate, alkoxytri(meth)acryloyl titanate, where alkoxy is $CH_3O—(C_2H_4O)_2$, and also the corresponding silicon compounds, etc. These compounds are available from the company Kenrich Petrochemicals, Inc., Bayonne, USA, or may be prepared in a manner known to the skilled worker.

By adding metal alkoxides in which at least one valence of the metal is satisfied by a radical other than an alkoxide it is possible to introduce further organic radicals bonded to Me. Compounds which may be used for this purpose are, for example, isopropyl triisostearoyl titanate, isopropyl tri (dodecyl)benzenesulfonyl titanate, isopropyl tri(dioctyl) phosphatotitanate, isopropyl(4-amino)benzenesulfonyl di(4-dodecyl)benzenesulfonyl titanate, isopropyl tri(dioctyl) pyrophosphatotitanate, isopropyl tri(N-ethylenediamino) ethyl titanate, di(dioctyl)pyrophosphate-oxoethylene titanate, di(dioctyl)phosphato-ethylene titanate, di(dioctyl) pyrophosphato-ethylene titanate, di(butyl,methyl) pyrophosphato-ethylene titanate, tetraisopropyl di(dioctyl) phosphatotitanate, tetraoctyl di(ditridecyl)phosphitotitanate, tetra(2,2-diallyloxymethyl)butyl di(ditridecyl) phosphitotitanate, dimethacryloyl-oxoethylene titanate, neoalkoxy-trineodecanoyl titanate, neoalkoxy-tri(dodecyl) benzenesulfonyl titanate, neoalkoxy-tri(dioctyl) phosphatotitanate, neoalkoxy-tri(dioctyl) pyrophosphatotitanate, neoalkoxy-tri(N-ethylenediamino) ethyl titanate, neoalkoxy-tri(m-amino)phenyl titanate, and the corresponding zirconium compounds. These compounds are also available from Kenrich Petrochemicals, Inc.

The particles of the invention are outstanding backbone polymers and backbone binders and form a novel and innovative class of substance. They may be formulated, alone or with coreactants, for the preparation of coating, polymer, molding, casting, adhesive and sealing compositions, surface coating materials, antireflection coating compositions, compositions for the dental, cosmetic and medical areas, and/or as binders for woodbase materials and stone compositions and the like. Such formulations may be modified with customary auxiliaries, such as additives, such as elasticizing tougheners, light stabilizers and aging inhibitors, plasticizers, lubricants, antistats, adhesion promoters organic and inorganic fillers and reinforcing agents, such as calcium carbonate, kaolin, light and heavy spars, silicon oxides, alkaline earth metal oxides, metal oxides and metal powders, hollow microstructures, carbon blacks, woodflours, fibers of α-cellulose, glass, polyamide, polyester, graphite and carbon pigments and dyes, such as white pigments, titanium dioxide, pigmentary carbon blacks, azo pigments and the like.

The particles of the invention may be incorporated advantageously into coating compositions. The coatings and films obtained possess outstanding mechanical and physical properties, depending on the crosslinking density. For instance, the scratch resistance is improved significantly in comparison to materials obtained by the sol-gel process. The values for gas permeation, to oxygen and nitrogen, for example, are also markedly improved with films comprising the particles of the invention.

The incorporation of the particles has also resulted, in particular, in changes in viscoelastic parameters in comparison to the unmodified polymer samples. When a (polymeric) sample is subjected to harmonic cyclical stressing, the strain—as in many other physical cause/effect relationships—follows the mechanical cyclic stress with a time delay. The elasticity modulus E, which occurs in Hooke's law and is a measure of the resistance of materials to mechanical stresses (strength), is therefore to be applied in complex form (E'+iE"), the storage modulus E' and the loss modulus E" being dependent on temperature and frequency. Additionally, for the moduli E' and E", the dispersion relationships are manifested in analogy, for instance, to the complex variables of permeability and dielectric constant in Kramers-Kronig relationships.

The moduli E' and E" are to be determined by means of Dynamic Mechanical Thermoanalysis (DMTA). For this purpose, films, coats or else fibers are subjected to a harmonic exciter oscillation in the range from 0.01 to 200 Hz while at the same time being heated in accordance with a temperature program.

Derived characteristic material parameters obtained include the attenuation factor tan $\delta = E''/E'$ and the glass transition temperature Tg, above which the materials soften. The Tg is given by the position of the maximum loss modulus.

The results of the dynamic mechanical measurements can be found in the use examples. These results can be explained only by extremely efficient heterogeneous copolymerization between the extended surface regions of the reactive particles and the organic substrate (increase in the polymeric network density). This is accompanied by an above-average improvement in macroscopic properties such as, for example, high temperature stability, scratch and abrasion resistance, and also bond strength and gas barrier effect. In order to be able to estimate the effect of these results, it is necessary to refer to the investigations of other polymeric nanocomposites with incorporated polymerization-inactive particles (T. Lan, T. J. Pinnavaia, Chem. Mater. 6 (1994) 2216, W. Helbert, J. Y. Cavafile, A. Dufresne, Polym. Composites 17 (1996) 604), where a significant increase in the storage modulus was found only in the softening range above Tg. Moreover, in these systems, the glass transition temperature remains largely unaffected by the nanoglobular filler.

As a result of the incorporation of the particles by covalent bonding, there is a considerable increase in the storage modulus throughout the temperature range measured.

The results of this are temperature stabilities and bond strengths of up to 600° C. or more, extreme scratch and abrasion resistances, pronounced barrier effects with respect to gases, such as nitrogen and oxygen, and also good adhesive bond strengths, in addition to high chemical, long-term and aging stability.

The particles of the invention may be foamed both alone and with coreactants. Such foams may be produced using known chemical blowing agents, such as azo compounds, azodicarboxamides, hydrazine derivatives, semicarbazides, and gases, such as nitrogen, carbon dioxide, hydrogen peroxide, and other organic and inorganic per compounds, and also expansion agents, such as calcium carbide, for example, which form gases on contact with water.

The foams produced with the particles of the invention possess outstanding resistance properties in the event of fire, since they possess a high glass transition temperature and, owing to the large amount of inorganic constituents, are of only limited flammability or are completely nonflammable. Depending on the type of foam, in addition, a positive effect is produced by the very good insulation value in addition to the high temperature resistance. Moreover, at the interfaces between adherend surfaces and adhesive film, the particles develop very high adhesive forces without detracting from the cohesive strength of the cured adhesive film, even at high temperatures.

If the particles have groups comprising phosphorus, improved corrosion and water resistance is achieved.

In addition, it has been found that, when the particles of the invention are used in compositions, there is surprisingly no need for rheology-improving additives or, in the case of mineral-filled systems, thixotropic agents and antisedimentation agents. The transparency of the compositions is not adversely affected even at high particle contents.

EXAMPLES

The examples illustrate the invention without restricting it.

The definitions of the abbreviations used in the examples are as follows:

Particle Core A

| Raw material | Abbreviation | Particle size (average) | BET surface area (DIN 6613 1) $m^2/g$ |
|---|---|---|---|
| Highly disperse silicon dioxide | HDK 600 | 40 nm | 200 ± 50 |
| | HDK 100 | 0.5 mm | — |
| Mixed oxide (98.3% $SiO_2$ + 0.3–1.3% $Al_2O_3$) | HDK 80 | 30 nm | 80 ± 0 |
| Aluminum oxide | HDA | 13 nm | 100 ± 15 |
| Titanium dioxide | HDT | 21 nm | 50 ± 15 |

Particle Side Chains B—X

| Raw material | Abbreviation |
|---|---|
| Methacryloyloxypropyl-trimethoxysilane | MEMO |
| 3-Aminopropyl-trimethoxysilane | APMO |
| Vinyltrimethoxysilane | VTMOS |
| Vinyltriethoxysilane | VTEOS |
| Oligomeric, alumosiloxane-modified methacryloyloxy-propyl trimethoxysilane | MEMO AL |
| Polymethyl-H-siloxane containing about 40 —Si—H groups | MH 15 |
| Aluminum isopropoxide, 97% by weight | ALUPROP |
| Glycidyl methacrylate | GMA |
| Zirconium(IV) ethoxide | ZIRKO |

Comonomer/Reactive Solvent for Particles

| Raw material | Abbreviation |
|---|---|
| Tetraethoxypentaerythritol tetraacrylate | Mo 10 |
| Bisethoxy-bisphenol A-diacrylate dissolved in tripropylene glycol diacrylate | Mo 20 |
| Trisethoxy-trimethylol propane triacrylate | TETMPTA |
| 4'-(1',2'-epoxycyclohexyl)methyl 1,2-epoxycyclohexane-4-carboxylate | Mo 30 |
| Trimethylolpropane triacrylate | TMPTA |
| Trisethoxy-2,4,6-triamino-s-triazine triacrylate | Viaktin 5970 |

Miscellaneous

| | |
|---|---|
| Wetting agent | aqueous sodium dodecyl sulfate solution, 30% strength by weight |
| Catalyst | aqueous methanesulfonic acid, 70% strength by weight (Examples 1–11) |

-continued

| | |
|---|---|
| | maleic acid or maleic anhydride (Examples 12–16) |
| pbw | parts by weight |
| EBC | electron beam curing |

Preparation

The formulations of Examples 1 to 15 are summarized in Table 1.

Examples 1 to 15

The raw materials and compositions of the particles of the invention are evident from Table 1, while the preparation is described below.

The respective comonomer is charged to a stirred vessel and heated to the predetermined reaction temperature. When the reaction temperature has been reached, the stated amounts of core material A and the compounds B—X are introduced alternately into the liquid comonomer with intensive stirring and are distributed homogeneously. Subsequently, water and the amounts of wetting agent and catalyst as per Table 1 are added with stirring over 15 minutes. Subsequently, stirring is continued at the respective reaction temperature. Finally, the reaction mixture is neutralized, if appropriate, with 50% strength aqueous sodium hydroxide solution over about 15 minutes and the reaction mixture is cooled to room temperature. In Example 11, there is no need for an initial comonomer charge. In this case, MH 15 is introduced as initial charge.

Example 16

A stirred vessel (2l) equipped with stirrer, dropping funnel and reflux condenser is charged with 100 pbw of HDK 600 and/or HDA in 1 l of acetone. The mixture is heated at boiling with intensive stirring. Then, with stirring continuing, 50 pbw of MEMO followed by 1.5 pbw of maleic anhydride dissolved in 10 pbw of water are added. Heating is continued for 2 hours under reflux. Finally, the solvent is distilled off under reduced pressure (1.6 kPa) at 30° C. The resulting nanopowder is subsequently comminuted or micronized. The yield is virtually quantitative.

Example 17

30.0 pbw of HDK 100 were pasted up in 10.0 pbw of GMA and subsequently mixed with 60.0 pbw of a mixture consisting of 12% by weight TMPTA and 88% by weight TETMPTA. This mixture is ground in a Fritsch planetary ball "Pulverisette 5" using zirconium(IV) oxide beads (4 beads Ø 20 mm; 15 beads Ø 10 mm; milling beaker volume 75 ml) at a milling beaker rotational speed of 360 min$^{-1}$ for 45 minutes. Subsequently, 0.2 ml of 70% strength aqueous perchloric acid is added dropwise to effect covalent attachment to the core material A by way of the epoxy group of the GMA. After further milling for approximately 20 minutes, the colloidal dispersion obtained may be processed in accordance with known methods. Regarding its properties, see Table 2.

Example 18

In a stirred vessel with mounted reflux condenser, 46 pbw of HDK 600 and 34 pbw of MEMO are dissolved in 200 pbw of acetone and heated to boiling. Subsequently, 20 pbw of ALUPROP are metered in very quickly with intensive stirring. After about 5 minutes, 13 pbw of water, 2.45 pbw of wetting agent solution and 1.3 pbw of catalyst solution are added over the course of 15 minutes. At 56° C., stirring is continued for one hour. Subsequently, the reaction mixture is neutralized, if appropriate, with 50% strength sodium hydroxide solution and the inert solvent is distilled off under reduced pressure. At room temperature, the pure reaction mass is semisolid to solid and possesses thermoplastic properties.

TABLE 1

Compositions (formulations) of Examples 1 to 15

| Example | Comonomer reactive solvent pbw | Core material A pbw | Side chains B-X pbw | Water pbw | Wetting agent + catalyst solution | Reaction temperature ° C. | Reaction duration min |
|---|---|---|---|---|---|---|---|
| 01 | 66.25 Mo 20 | 22.5 HDK 600 | 11.25 MEMO | 2.9 | 0.54 + 0.50 | 80 | 105 |
| 02 | 62.5 Mo 10 | 17.5 HDK 600 | 12.5 MEMO + 7.5 ALUPROP | 4.875 | 0.92 + 1.00 | 80 | 105 |
| 03 | 39.75 Mo 30 + 26.50 TMPTA | 22.5 HDK 600 | 11.25 MEMO | 2.9 | 0.54 + 0.50 | 60 | 75 |
| 04 | 66.25 Mo 20 | 22.5 HDK 600 | 11.25 MEMO | 2.8 | 0.54 + 2.0 | 66 | 150 |
| 05 | 62.5 Mo 10 | 17.5 HDK 600 | 12.50 MEMO + 7.50 ALUPROP | 4.58 | 0.92 + 2.0 | 70/78 | 30 |
| 06 | 62.5 Mo 10 | 25.0 HDK 600 | 12.5 MEMO AL | 1.25 | 0.236 + 0.200 | 80 | 90 |
| 07 | 66.25 Mo 30 | 22.5 HDK 600 | 11.25 MEMO AL | 1.45 | 0.270 + 0.250 | 60 | 30 |
| 08 | 62.50 Mo 10 | 17.5 HDK 600 | 12.5 MEMO AL + 7.5 ZIRKO | 1.9 | 0.350 + 0.250 | 80 | 90 |
| 09 | 66.25 Mo 30 | 22.5 HDK 600 | 11.25 APMO | 1.65 | 0.230 + 0.250 | 60 | 20 |
| 10 | 62.5 Mo 10 | 17.5 HDK 80 | 11.25 MEMO AL + 8.75 ZIRKO | 1.9 | 0.360 + 0.250 | 80 | 90 |
| 11 | | 20.0 HDK 600 | 80.0 MH 15 | 2.9 | 0.528 + 1.000 | 80 | 50 |
| 12 | 62.5 Mo 10[1] | 25.0 HDK 600 | 12.5 VTMOS | 5.0 | 0.250 + 0.375[3] | 70 | 180 |
| 13 | 64.5 Mo 10[2] | 25.7 HDK 600 | 9.8 VTEOS | 3.1 | 0.150 + 0.390[3] | 70 | 270 |
| 14 | 55.5 Mo 30[1] | 22.3 HDA | 22.2 VTMOS | 8.9 | 0.440 + 0.330[3] | 70 | 180 |
| 15 | 55.5 Mo 20[1] | 22.3 HDT | 22.2 VTMOS | 8.9 | 0.440 + 0.330[3] | 70 | 180 |

[1]Addition of 0.04 pbw of 4-hydroxyanisol
[2]Addition of 0.12 pbw of 4-hydroxyanisol
[3]Maleic acid or maleic anhydride as catalyst instead of methane sulfonic acid Comparative Example 1

"Sol-gel Process":

A three-necked flask with stirrer and gas passage line is charged with 40 ml of TMPTA. Following an hour of vigorous blanketing with pure nitrogen, a solution consisting of 0.5 pbw of sodium in 10 ml of absolute ethanol is added over the course of 5 minutes. After further stirring for 10 minutes, 7.5 ml of anhydrous 2-aminoethanol are metered in over the course of 20 minutes. Subsequently, stirring is continued at 50° C. for 4 hours, with $N_2$ being introduced and passed through continuously. Thereafter, 10 ml of ethyl orthosilicon dioxidete are added over the course of 15 minutes. A solution of 0.25 g of wetting agent (sodium dodecyl sulfate dissolved in 5 ml of water) is then added dropwise to the reaction mixture over the course of one hour. Stirring is continued at 50° C. for a further hour. Finally, the batch is cooled to room temperature as quickly as possible. This reaction product was tested in comparison with the particles of the invention (Table 3).

Comparative Example 2
"Sol-gel Surface Coating Material"

A stirred vessel is charged with 33 pbw of TMPTA and 0.08 pbw of 4-hydroxyanisol and this initial charge is heated to 65–70° C. To the preheated acrylate mixture there is added a solution of 0.2 pbw of maleic anhydride, 0.7 pbw of sodium dodecyl sulfate and 14.0 pbw of water, followed by a mixture of 45.5 pbw of tetraethoxysilane and 6.5 pbw of MEMO, which is added over the course of 30 minutes. Subsequently, the reaction mixture is stirred further and the water/alcohol mixture is distilled off at a pressure of 1.6 kPa over the course of 6 hours. Finally, the remaining reaction mass is cooled very quickly to room temperature.

Use Examples 19–21

Example 19

Figure 1:
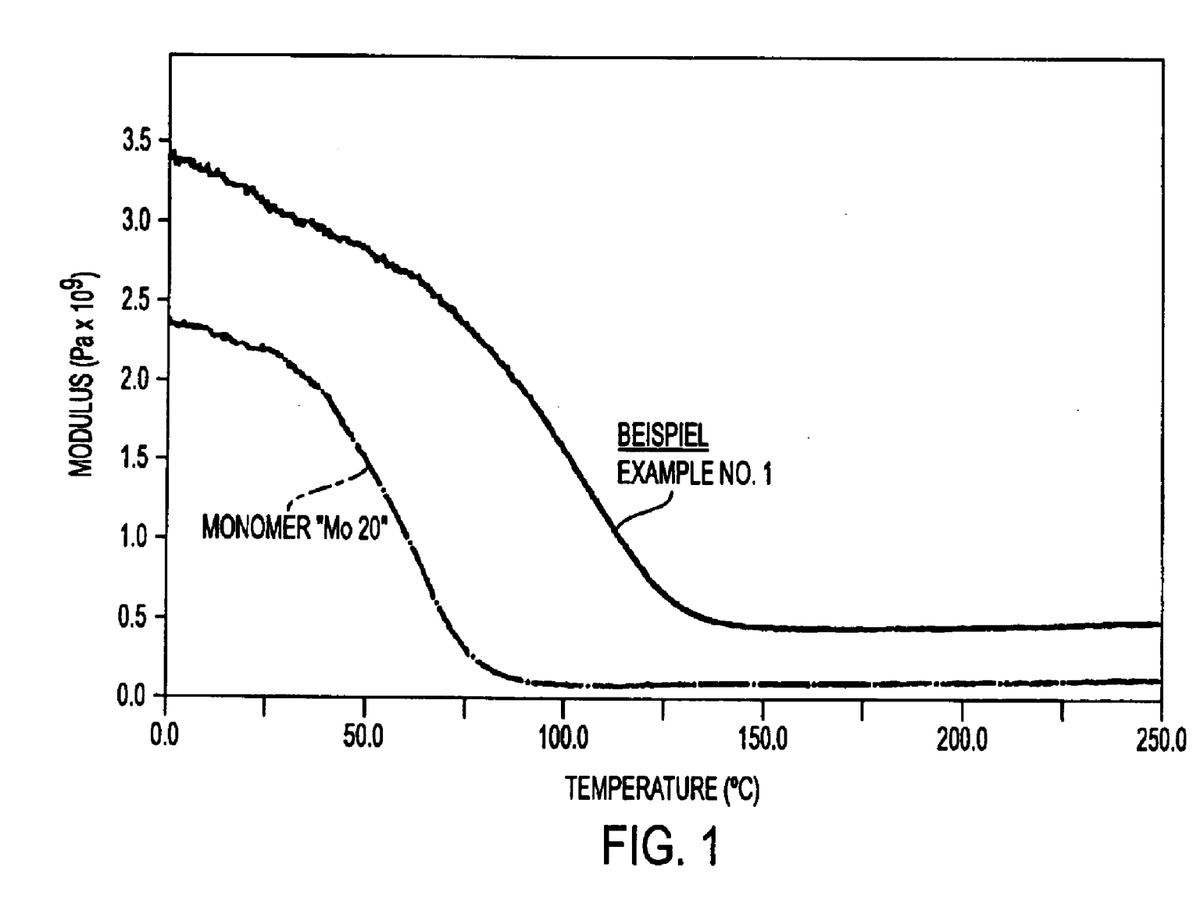
FIG. 1 is a graph showing an increase in storage modulus for particles of the invention.
Figure 2:
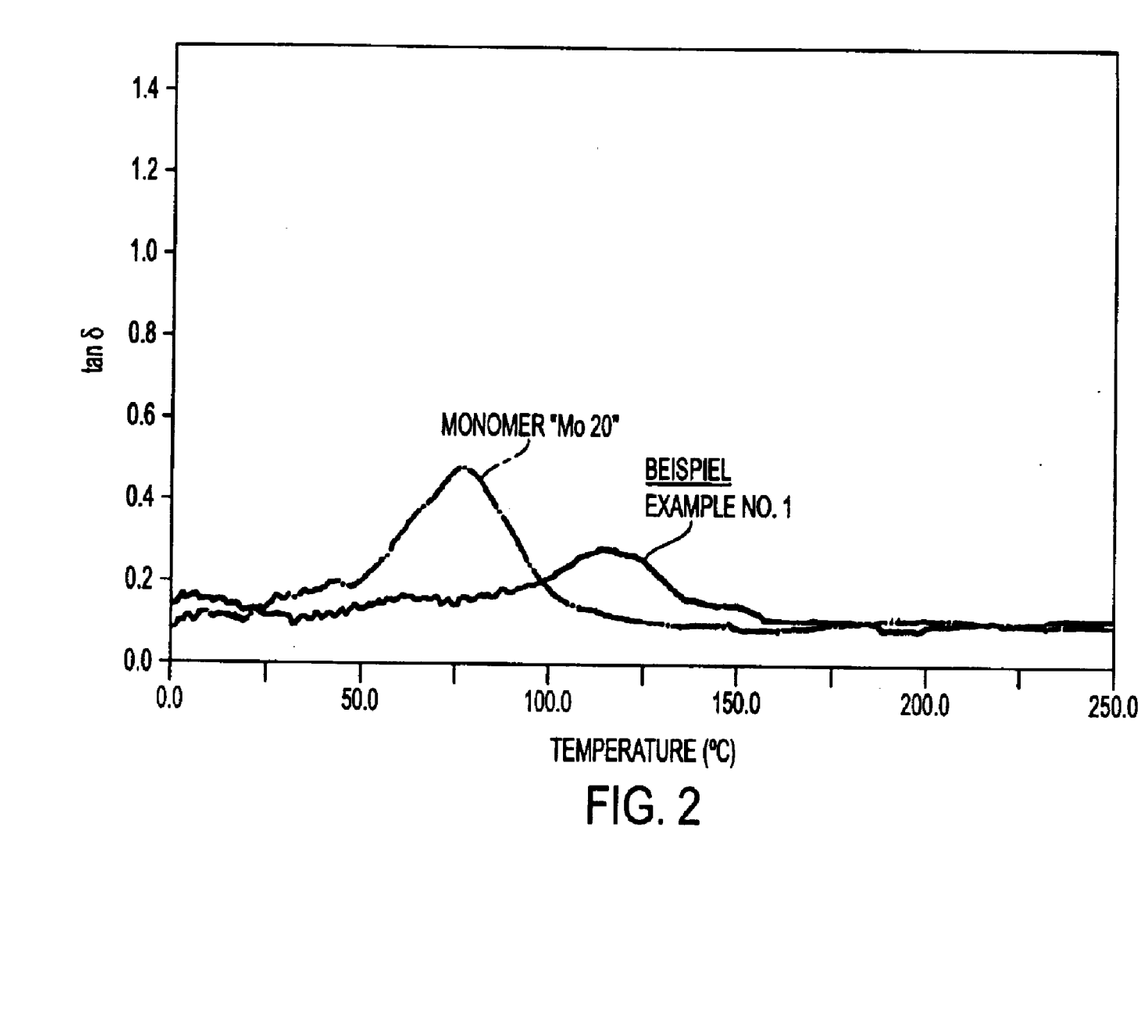
FIG. 2 is a graph showing a higher glass transition temperature in accordance with the present invention.

Using the colloidal dispersion from Example 1 and a coating bar, a film approximately 0.1 mm thick was produced on a silicone release paper. This film was subsequently cured with electron beams (dose 80 kGy/180 keV unit) under an inert gas atmosphere ($N_2$). This film was subjected to dynamic mechanical thermoanalysis (DMTA) in order to determine the attenuation factor tan $\delta=E''/E'$ and the glass transition temperature (Tg). The measurements were conducted using the Perkin Elmer unit DMA 7e with applied statistical and dynamic exciter forces of 200 mN at a frequency of 1 Hz in the temperature range from −20 to +250° C. In FIG. 1 it can be seen that the storage modulus for the particles of the invention is markedly increased in comparison to the straight acrylate "Mo 20" even in the solidification range lying below Tg (being increased by a factor of approximately 1.4 at 20° C.). In the mechanical dispersion region, there is a shift in the maximum of tan $\delta$, and the glass transition temperature ($T_g$) is higher by several 10 K (FIG. 2).

Example 20

Figure 3:
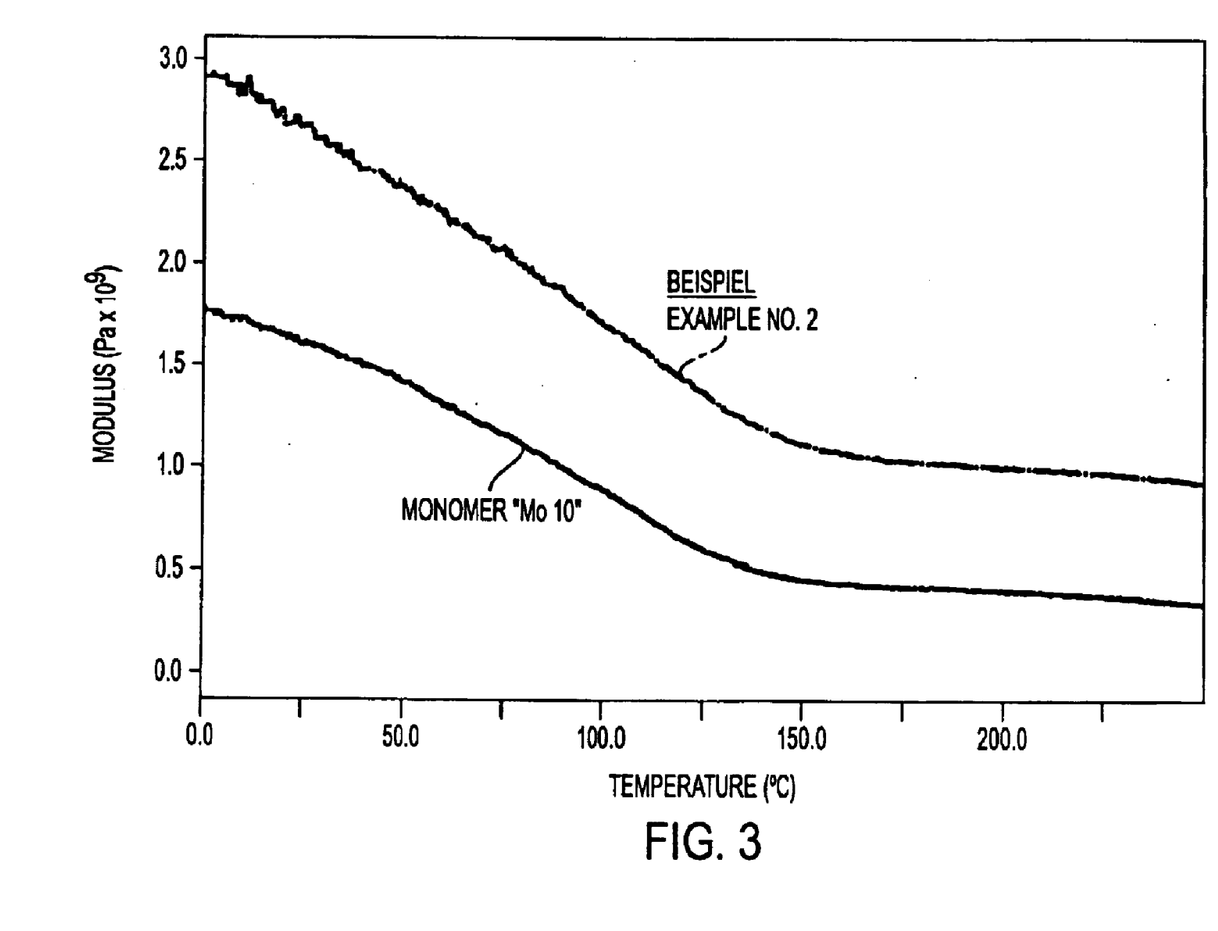
FIG. 3 is a graph showing higher temperature stability of storage modulus in accordance with the present invention.

The procedure of Example 19 was repeated using the colloidal dispersion from Example 2 and a test film was produced. The only difference between these dispersions is their comonomers. The replacement of the comonomer "Mo 20" (Example 1) by the comonomer "Mo 10" on its own demonstrates, in accordance with the invention, a further improvement in the viscoelastic and macroscopic properties, which is achieved by the modification of the highly crosslinking tetraacrylate "Mo 10" and which no longer possesses a glass transition. Even for the unmodified organic substrate, FIG. 3 shows a much higher temperature stability of the storage modulus in comparison to "Mo 20" in Example 1 (FIG. 1).

Figure 4:
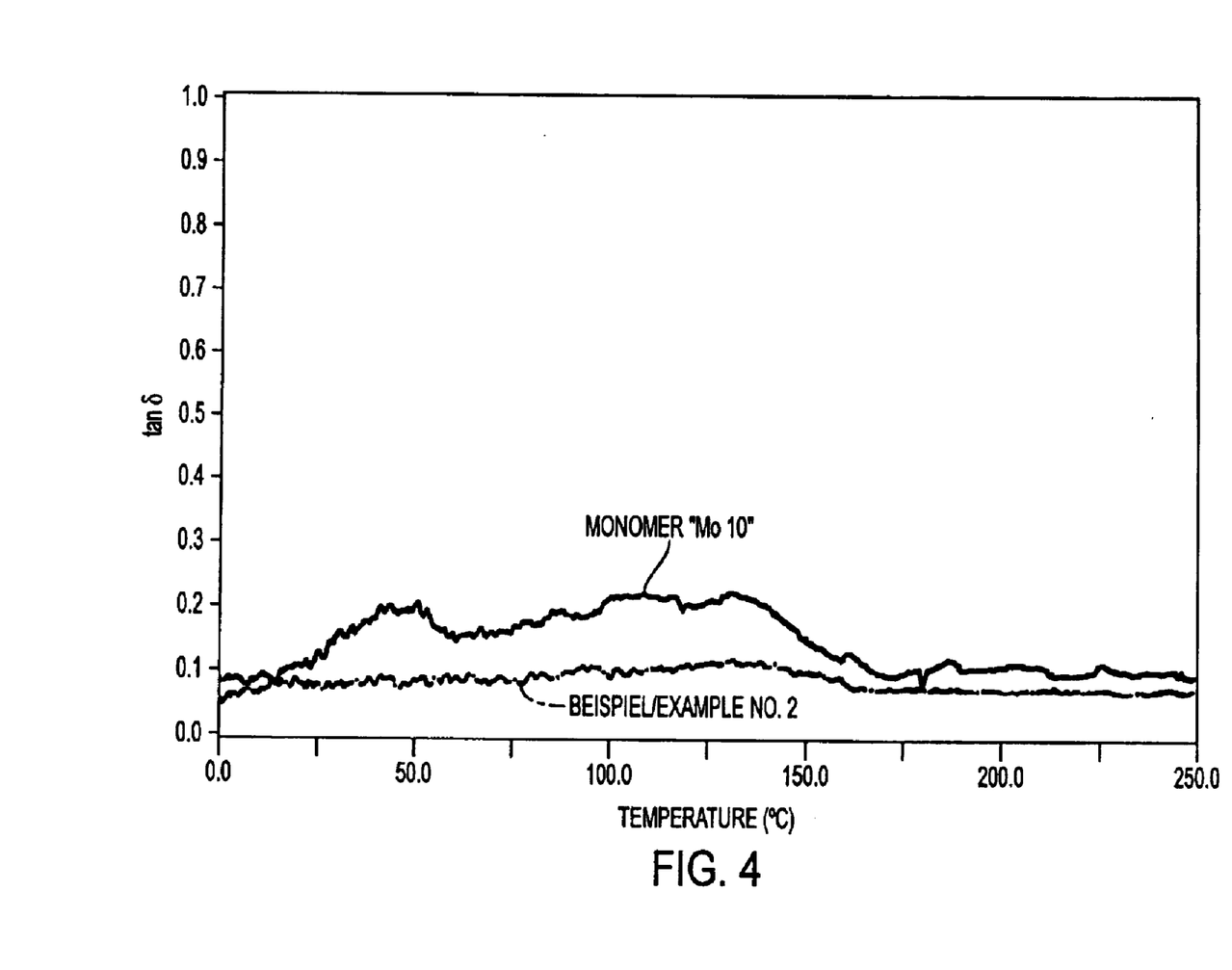
FIG. 4 is a graph showing high temperature resistance in accordance with the present invention.

As a result of the incorporation by covalent bonding of the particles of the invention (Example 2), there is a considerable increase in the storage modulus throughout the measured temperature range measured. Therefore, temperature stabilities of 600° C. or more, extreme scratch and abrasion resistances, pronounced barrier properties with respect to gases, such as nitrogen and oxygen, and also good adhesive bond strengths, as well as high chemical, long-term and aging stabilities, are provided and are realizable (FIG. 4). Further properties in comparison to the monomer "Mo 10" in Comparative Example 1 (sol-gel process) are summarized in Table 3.

Example 21

Using the colloidal dispersion from Example 2, an adhesive having the following composition was formulated:

50.0 pbw of reactive dispersion from Example 2

44.0 pbw of calcium carbonate filler, coated 5.0 pbw of dibenzoyl peroxide paste, 50% strength in dioctyl phthalate 1.0 pbw of N,N'-diethylaniline First of all, the N,N-diethylaniline (accelerator) is distributed homogeneously in the reactive dispersion. Subsequently, the filler is incorporated homogeneously at slightly elevated temperature (40° C.). Finally, the reaction initiator—benzoyl peroxide paste—is added and is uniformly distributed in the paste. The finished adhesive has a pot life (DIN 16920) of 25 minutes/20° C. This adhesive was used to bond degreased steel test specimens in incised overlap for the tensile shear test in accordance with DIN 53283. After 24-hour storage of 10 test specimens at room temperature, they were divided; that is, 5 of these test specimens were stored in a drying oven at 200° C. for 48 hours and then stored at room temperature for 24 hours. The subsequent test to DIN 53283 gave the following average values:

| Tensile shear strength | |
| --- | --- |
| Curing 24 h/20° C. | 18 N/mm$^2$ |
| Curing 24 h/20° C. and Aging 48 h/200° C. | 17 N/mm$^2$ |

The high glass transition temperature of the cured particle dispersion (FIG. 4) confirms the high temperature resistance of such compositions without any need to accept a loss in bond strengths. The adhesive film showed a 100% cohesive fracture.

TABLE 2

Hardness, scratch and abrasion resistance of the coating according to Example 12 in comparison to 2 commercial products

| Product | EBC dose [kGy] | Pendulum hardness [S] | Erichsen indentation[1] [N] | Vicardt diamond needle[2] [N] | Taber Abraser falling sand method [~10% - total] |
| --- | --- | --- | --- | --- | --- |
| Esa Lux LR 1283 (commercial product) - comparative - | 90 | 142 | 14/16 NH[3] | 2 | 1400–3300 U |

TABLE 2-continued

Hardness, scratch and abrasion resistance of the coating according to Example 12 in comparison to 2 commercial products

| Product | EBC dose [kGy] | Pendulum hardness [S] | Erichsen indent-ation[1] [N] | Vicardt diamond needle[2] [N] | Taber Abraser falling sand method [~10% - total] |
|---|---|---|---|---|---|
| Viaktin 5970 (commercial product) - comparative - | 140 | 121 | — | — | 1500–2500 U |
| Example 19 inventive | 60 | 144/152 NH[3] | >20 | 8 | 4500–9500 U |

[1]Erichsen = steel panel
[2]Vicardt = diamond
[3]NH = aftercuring after 12 days

TABLE 3

Property comparisons with prior art products, sol-gel process products, and products of Example 2 (inventive)

| Product | EBC dose [kGy] | Micro-scratch hardness (diamond) [N] | Erichsen hardness DIN 55350 (test rod 318) [N] | Taber Abraser test test DIN EN 438-2 [U] | Gloss incident angle DIN/ISO 900ff 60° C[1] | Gas permeation[2] ml/h × m² × bar DIN 53380 | | Separation factor |
|---|---|---|---|---|---|---|---|---|
| | | | | | | $N_2$ | $O_2$ | |
| Monomer Mo 10 | 40 | 3.5 | 4 | 2700 | 75.0/39.8 | 8.4 | 22.3 | 2.7 |
| Comparative Example 1 "sol-gel process | 40 | 5.0 | 5.5 | 5200 | 68.0/54.9 | 4.3 | 17.2 | 4.0 |
| Example 2 inventive | 40 | 8.0 | 7.5 | 8300 | 81.6/80.4 | 1.1 | 7.8 | 7.1 |

[1]Initial value and after 60 manual scratch cycles with steel wool
[2]Paper (60 g) Application weight 15 g/m²

What is claimed is:

1. High temperature resistant polymerizable metal oxide particles having a glass transition temperature of ≧100° C. and having a core A comprising at least one oxide of a metal or semimetal from main groups three to six, transition groups one to eight of the periodic system, or the lanthanides and having at least one side-chain group —(B)$_w$—X, which is bonded covalently to the core by way of one or more oxygen atoms of the oxide, w being 0 or 1 and B being a radical of the formulae —(MeO)$_x$Me(O)$_{y1}$—(R)$_{y2}$— or —R(O)$_z$— in which x is from 0 to 100, y1, y2 and z independently of one another are 0 or 1, and Me is a metal or semimetal from main groups three to six or transitions groups three to eight of the periodic system, the free valences of Me representing a bond to a further oxygen atom of the core A and/or a bond via an oxygen atom to an Me in another group B or and/or a bond to an oxygen atom of another core A and/or being satisfied by H, an organic radical and/or a trialkylsilyloxy radical;

R is divalent alkyl, cycloalkyl, aryl, arylalkyl, alkylaryl, alkoxy, acyl, acyloxy or a radical remaining following the removal of two phenolic hydrogen atoms from a phenol compound having at least two phenolic hydrogen atoms from a phenol compound having at least two phenolic hydroxyl groups, it being possible for R to be substituted, if desired, by 1, 2, or 3 radicals selected independently of one another from hydroxy, alkoxy, halogen and also, in the case of aryl or cycloalkyl radicals, alkyl, and/or interrupted in the chain by one or two oxygen atoms, and X is a reactive functional group or a radical containing a reactive functional group, and whereby X may be attached to B through link Z, where Z is either O, NR², where R² is either H, $C_1$–$C_4$ alkyl, OCO, COO, NHCO, or CONH, and wherein the group or groups —(B)$_w$—X account for at least 10% by weight, based on overall weight of the particles.

2. The particles as claimed in claim 1, where the group or groups —BX account for at least 20% by weight, based on the overall weight of the particles.

3. The particles as claimed in claim 1, where the core is an Si, Al, Ti or Zr oxide, or a mixture or mixed oxide thereof.

4. The particles as claimed in claim 1, where Me is a metal or semimetal from main group three or four or transition group four of the periodic system.

5. The particles as claimed in claim 4, where Me is Si, Ti, Al or Zr.

6. The particles as claimed in claim 1, where B is selected from a) —Me (O)y1—R—
b) —Me—O—Me(O)y1—R—
c) —Me—O—Me—O—Me(O)y1—R—
d) —R—O—
e) —R— in which y is 0 or 1 and R has the definitions indicated in claim 1.

7. The particles as claimed in claim 6, where —Me—O—Me— in the radical B is selected from

—Si—O—Si—
—Si—O—Al—
—Si—O—Ti—
—Si—O—Zr—
—Al—O—Ti—
—Al—O—Zr—
—Al—O—Al— and —Me—O—Me—O—Me— in the radical c is —Si—O—Ti—O—Zr—.

8. The particles as claimed in claim 1, where R is divalent alkyl, hydroxyalkyl, alkoxy or acyloxy or a bisphenol A, B or F radical which remains following removal of the two phenolic hydrogen atoms.

9. The particles as claimed in claim 1, where X is an epoxy group, isocyanate group, a group having at least one active hydrogen atom or a group having at least one ethylenically unsaturated double bond.

10. The particles as claimed in claim 9, where X is an epoxy group, an amino group or a group of the formula or in which $R^1$ is the radical of an ethylenically unsaturated $C_3$–$C_8$ monocarboxylic acid or $C_4$–$C_8$ dicarboxylic acid that remains following removal of the carboxyl group and Y is O or $NR^2$, $R^2$ and $R^3$ being H or $C_1$–$C_4$ alkyl.

11. The particles as claimed in claim 10, where R is —(CH2)n—, —CH2—CHOHCH2— or CH2CHOHCH2—Z—, in which n is from 1 to 6 and Z is a bisphenol radical which remains following removal of the two phenolic hydrogen atoms.

12. The particles as claimed in claim 1, where A is silicon dioxide, titanium dioxide or an Si/Al mixed oxide, —B—X is $(MeO)_x Me(O)_{y1}(CH_2)_n OCOCR^4{=}CH_2$ or $(MeO)_x Me(O)_{y1} CH_2 CHOHCH_2 OCOCR^4{=}CH_2$, where Me is Si, Al, Ti or Zr, x is 1 or 2, y1 is 0 or 1, n is from 2 to 6 and $R^4$ is H or $CH_3$, the free valences of Si, Al, Ti or Zr being satisfied by alkoxy radicals and/or bonded to oxygen atoms of the same or a different core A.

13. The particles as claimed in claim 12, where MeOMe or MeOMeOMe has the definitions indicated in claim 7.

14. The particles as claimed in claim 1, where the free valences of Me are satisfied by alkyl, aryl, alkoxy, a group of the formula in which $R^1$ and Y have the definitions indicated in claim 10, or a group comprising phosphate.

15. The particles as claimed in claim 1, where the side chain is a polyalkyl hydrosiloxane radical.

16. The particles as claimed in claim 1 having a glass transition temperature of the homopolymers of >250° C.

17. A process for preparing the particles as claimed in claim 1, characterized in that the radicals B, —B—X and/or X are attached by covalent bonding to the core A, present in solid form, in the presence of strong acids.

18. The process as claimed in claim 17, characterized in that the covalent attachment is conducted in one process step (in situ).

19. A composition comprising the particles as claimed in claim 1.

* * * * *